United States Patent
Wu et al.

(10) Patent No.: US 9,232,485 B2
(45) Date of Patent: Jan. 5, 2016

(54) SYSTEM AND METHOD FOR SELECTIVELY COMMUNICATING WITH AN IMPLANTABLE MEDICAL DEVICE

(71) Applicants: Yongjian Wu, Saratoga, CA (US); Allan Schwartz, Thousand Oaks, CA (US)

(72) Inventors: Yongjian Wu, Saratoga, CA (US); Allan Schwartz, Thousand Oaks, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 111 days.

(21) Appl. No.: 13/974,448

(22) Filed: Aug. 23, 2013

(65) Prior Publication Data
US 2015/0056921 A1    Feb. 26, 2015

(51) Int. Cl.
*H04B 7/00* (2006.01)
*H04W 52/42* (2009.01)
*H04W 4/00* (2009.01)
*H04B 13/00* (2006.01)
*G06Q 50/22* (2012.01)

(52) U.S. Cl.
CPC ............... *H04W 52/42* (2013.01); *G06Q 50/22* (2013.01); *H04B 13/005* (2013.01); *H04W 4/008* (2013.01)

(58) Field of Classification Search
CPC ........................................................ H04B 5/02
USPC .............................. 455/41.2, 67.11, 574, 66.1
See application file for complete search history.

(56) References Cited

U.S. PATENT DOCUMENTS

| | | | |
|---|---|---|---|
| 7,502,594 B2* | 3/2009 | Ginggen | G06K 7/0008 455/126 |
| 9,186,519 B2* | 11/2015 | Kivi | A61N 1/37276 |
| 2003/0220673 A1* | 11/2003 | Snell | A61N 1/08 607/60 |
| 2006/0246846 A1* | 11/2006 | Ginggen | G06K 7/0008 455/69 |
| 2008/0055070 A1* | 3/2008 | Bange | A61N 1/37252 340/539.12 |
| 2008/0255629 A1* | 10/2008 | Jenson | A61B 5/1107 607/19 |
| 2012/0265271 A1* | 10/2012 | Goetz | A61N 1/37247 607/59 |
| 2013/0238048 A1* | 9/2013 | Almendinger | A61N 1/0509 607/40 |
| 2014/0266774 A1* | 9/2014 | Greene | A61N 1/37276 340/870.01 |

* cited by examiner

*Primary Examiner* — April G Gonzales
(74) *Attorney, Agent, or Firm* — Thersa A. Raymer

(57) ABSTRACT

A system may include a target implantable medical device (IMD) and an external device configured to selectively communicate with the target IMD. The external device may include a communication module configured to communicate with the target IMD, a response analysis module configured to receive and analyze a target response signal from the target IMD and other response signals from other IMDS, and a power adjustment module configured to receive one or more power-adjustment request signals from the response analysis module. The power adjustment module is configured to adaptively adjust a power of a transmission request over a first frequency band based on the one or more power-adjustment request signals until the response analysis module receives only the target response signal from the target IMD.

22 Claims, 12 Drawing Sheets

SYSTEM AND METHOD FOR SELECTIVELY COMMUNICATING WITH AN IMPLANTABLE MEDICAL DEVICE

BACKGROUND OF THE DISCLOSURE

Embodiments of the present disclosure generally relate to implantable cardiac devices, and more particularly to implantable medical devices that communicate with an external device through radio frequency (RF) signals.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue (collectively hereafter "tissue") for diagnostic or therapeutic purposes.

Various IMDs are monitored by a programmer, such as remote care or base station, which is remotely located from the IMDs. For example, a patient may have an IMD that communicates with a base station within the patient's home. The base station may be located by a patient's bedside. The base station receives data from the IMD regarding the patient's physiological state and/or the operation state of the IMD. Based on the received data, the base station may convey the data to a remote server of a medical care network, or adjust operating parameters for the IMD. For example, the base station may adjust operating parameters of the IMD, such as when a patient experiences changes in arrhythmia, pacing, ST shift, various types of ischemia, base rate, and the like.

Many IMDs include an RF capability to communicate with the programmer. Data may be received from the base station when transmitted over varies frequency bands, such as at a 402-405 MHz frequency range, which represents the Medical Implant Communication Service (MICS) band. The MICS band enables a short-range, wireless link to be maintained between low-power implanted IMDs and an external programmer or base station.

An RF chip within a typical IMD periodically scans select frequency bands, such as the 2.45 GHz band, over the life of the IMD. The 2.45 GHz band is an unlicensed, microwave band. The IMD uses information received over the 2.45 GHz band to determine if the programmer is seeking to communicate with the IMD over another band (for example, the MICS band), which is used to receive and transmit data to and from the IMD. If the RF chip operating at a 2.45 GHz band detects that the programmer desires to communicate over the MICS band, the IMD then switches over to the MICS band. Bidirectional communication over the MICS band consumes substantially more power than the 2.45 GHz band. As such, through the use of the 2.45 GHz band, which is used to detect whether the programmer is attempting to communicate with the IMD, the IMD conserves energy. In general, the MICS band (for example, the 402-405 MHz band) affords a longer range and more robust connection than the 2.45 GHz band. However, as compared to the MICS band, the 2.45 GHz band draws less power from the IMD when scanning for connection requests and during a communications session.

In order to establish an RF communication link between a programmer and an IMD in some known systems, the programmer first establishes a short range inductive link with the IMD after an inductive wand is placed in proximity to the IMD. The programmer then sends an inductive telemetry command through the established inductive link to the IMD in order to initiate an MICS band RF scan for all allocated MICS band channels. The programmer then instructs the wand to establish an MICS band link with the IMD. Typically, the programmer assesses the channels and selects the clearest or least-interfered MICS channel from the available allocated MICS channels. The connection request is sent through the selected channels. When the RF chip in the IMD detects the connection request, the RF chip completes the MICS band link through coordinated actions between the RF chip and device firmware.

The communication connection process described above works well so long as the IMD, the wand, and the external programmer include inductive hardware. By default, the IMD typically does not perform a frequent scan on the MICS channel seeking a connection request, as doing so would deplete too much energy. Instead, the IMD scans the MICS channel after receiving a specific command from the programmer received over inductive hardware. As such, the IMD saves energy, which ensures longevity. At the same time, the programmer connects to a specifically-targeted IMD, because the inductive connection is typically targeted with a specific IMD at a short range.

However, with RF-only devices that do not include inductive hardware, the programmer may initiate a wake-up with multiple devices over the 2.45 GHz band. For example, if multiple IMDs are in close proximity with one another, each of the IMDs may be scanning the 2.45 GHz band and respond to a connection request from the programmer. Yet, the programmer may be targeting only a single IMD, but not multiple IMDs. As such, the programmer may erroneously wake up and communicate with non-targeted IMDs.

SUMMARY

Certain embodiments of the present disclosure provide an external device configured to selectively communicate with a target implantable medical device (IMD) within a vicinity of other IMDs. The external device may include a communication module configured to communicate with the target IMD with at least a transmission request, a response analysis module configured to receive and analyze a target response signal from the target IMD and the other response signals from the other IMDs, and a power adjustment module configured to receive one or more power-adjustment request signals from the response analysis module. The power adjustment module is configured to adaptively adjust a power of a transmission request over a first frequency band based on the one or more power-adjustment request signals until the response analysis module receives only the target response signal from the target IMD. The external device is configured to communicate with the target IMD over a second frequency band after the response analysis module receives only the target response signal.

The external device is configured to be positioned closer to the target IMD than the other IMDs. One or more of the communication module, the response analysis module, and the power adjustment module are contained within a wand that is configured to wake up the target IMD. Optionally, one or more of the communication module, the response analysis module, and the power adjustment module are contained within one or more of a patient home care system, a tablet, a smart phone, or a laptop computer.

The communication module may be an RF communication module that is devoid of telemetry hardware that is configured to facilitate inductive communication. The power adjustment module may be configured to incrementally decrease the power of the transmission request over the first frequency band when the response analysis module receives one or more of the other signals from one of more the other IMDs. Further, the power adjustment module may be configured to incrementally increase the power of the transmission request over the first frequency band when the response analysis module does not receive the target response signal. The first frequency band may be a low power, high frequency band, such as the unlicensed 2.45 GHz band. The second frequency band may be a high power, lower frequency band in the range of 402-405 MHz.

Certain embodiments of the present disclosure provide a system that may include a target implantable medical device (IMD), and an external device configured to selectively communicate with the target IMD.

Certain embodiments of the present disclosure provide a method of selectively communicating with a target implantable medical device (IMD) within a vicinity of other IMDs. The method may include communicating with the target IMD with a communication module, receiving a target response signal from the target IMD with a response analysis module, receiving one or more other response signals from one or more of the other IMDs with the response analysis module receive, and analyzing the target response signal and the one or more other response signals with the response analysis module. The method may also include receiving one or more power-adjustment request signals from the response analysis module at a power adjustment module, and adaptively adjusting a power of a transmission request over a first frequency band based on the one or more power-adjustment request signals until the response analysis module receives only the target response signal from the target IMD. The method may also include communicating with the target IMD over a second frequency band after the response analysis module receives only the target response signal.

DETAILED DESCRIPTION

Figure 1:
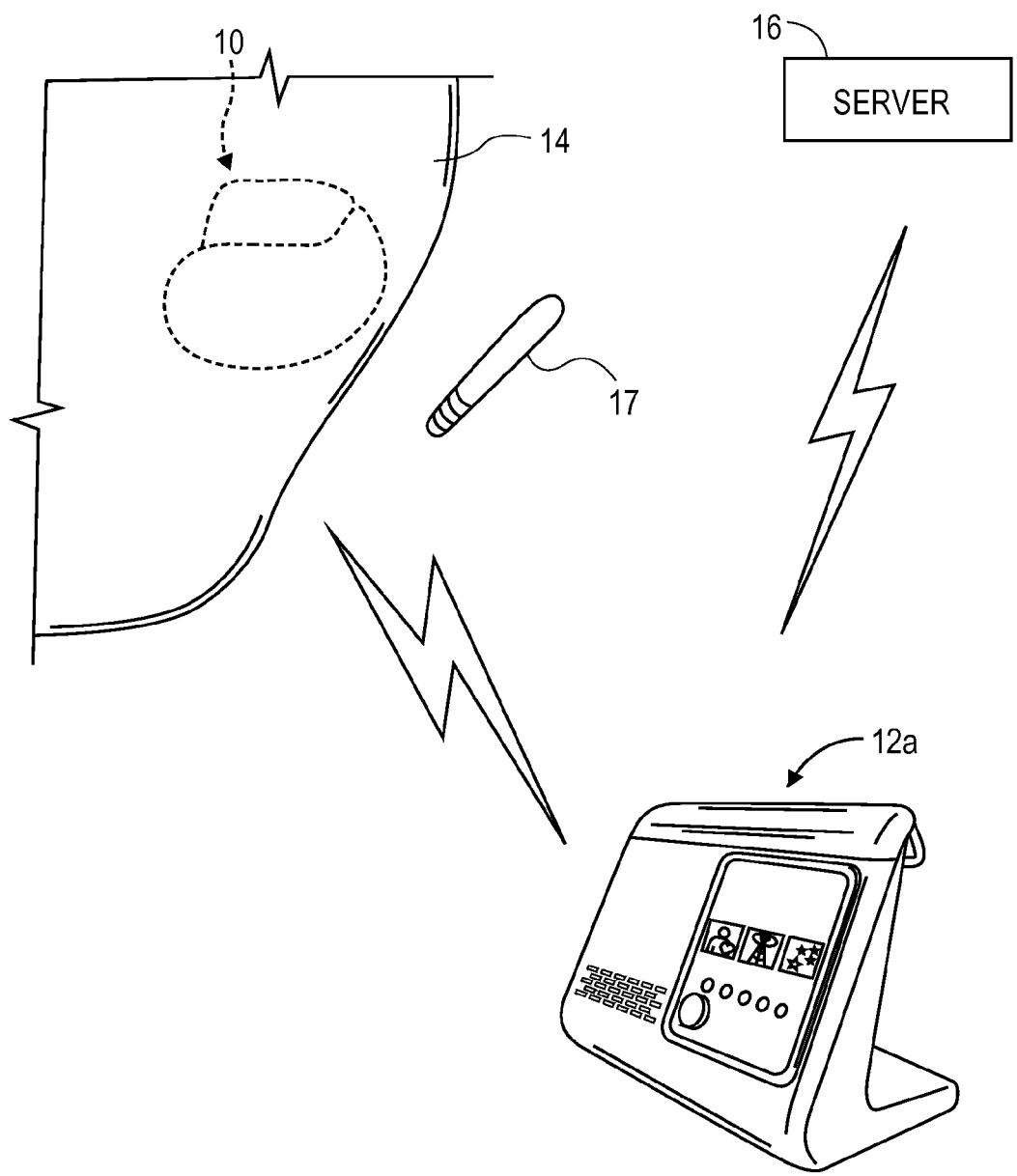
FIG. 1 illustrates a simplified view of an IMD and patient care system (PCS), according to an embodiment of the present disclosure.

FIG. 1 illustrates a simplified view of an IMD 10 and external programmer 12a, such as a patient care system (PCS), according to an embodiment of the present disclosure. The IMD 10 may be implanted within a patient 14. The remotely-located programmer 12a monitors the IMD 10. The programmer 12a may be located within a medical care facility, such as a hospital or clinic, or within a home of the patient 14, in his/her vehicle, at his/her office and the like. When the programmer 12a is located within the patient's home, the programmer 12a may be proximate to a bed of the patient 14. The programmer 12a functions as a base station that wirelessly communicates with the IMD 10. The programmer 12a may also communicate with a remote server 16 within a patient care network, such as over a phone link, cellular link, Internet connection, local area network, wide area network and the like.

The programmer 12a performs various functions, such as operating as an intermediate relay device to collect and store patient physiologic data, IMD operational status data and the like. The physiologic data may be electrical data related to a physiologic condition. The programmer 12a may then transmit the physiologic data, IMD operational status data and other data to the remote server 16 of the patient care network. Physicians and other personnel can monitor the patient and collect data over the patient care network. Also, the programmer 12a may receive updates, upgrades and other IMD control-related information from the patient care network and relay the IMD control-related information to the IMD 10.

The IMD 10 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

The programmer 12a may include a standalone antenna assembly. The programmer 12a may represent the Merlin® home patient care system offered by St. Jude Medical. The programmer 12a may include an RF telemetry subsystem that communicates with the IMD 10 and/or the server 16. The telemetry subsystem may include an RF telemetry circuit operatively connected to one or more MICS antennas. The telemetry circuit may also be operatively connected to a controller or processing unit. Alternatively, the programmer 12a may represent a handheld portable tablet-type programmer device used by physicians and others to communicate with, collect data from, program and reprogram the IMD 10. Also, alternatively, the programmer 12a may be a cell phone, personal computer, or laptop computer.

In operation, an RF chip within the IMD 10 periodically scans a first frequency band, such as a lower-power, high frequency band, such as a 2.45 GHz band, for example. The first frequency band may be an unlicensed, microwave band, such as the 2.45 GHz band. The IMD 10 uses information received over the first frequency band to determine if the programmer 12a is seeking to communicate with the IMD 10 over a second frequency band, such as a higher power, lower frequency band, such as the MICS band, which is used to receive and transmit data to and from the IMD 10. If the RF chip within the IMD 10 operating at the first frequency band detects that the programmer 12a desires to communicate over the second frequency band, the IMD 10 may switch over to the second frequency band.

A wand 17 may also be used to establish a communication link between the IMD 10 and the programmer 12a. The wand 17 may include an RF transmitter that transmits an RF wake-up call to the IMD 10 when in close proximity to the IMD 10. For example, the wand 17 may be positioned within 0-1 meters from the IMD 10 in order to wake the IMD 10 up so that a communication link between the IMD 10 and the programmer 12a may be established. Alternatively, the wand 17 may be able to wake the IMD 10 up at ranges longer than 1 meter. Once the wand 17 transmits an RF wake signal to the IMD 10, the IMD 10 may then switch from the first frequency band to the second frequency band in order to communicate with the programmer 12a. Also, the wand 17 may be configured to be removably connected to a handheld device, such as an iPhone, iPad, Kindle, and/or the like.

Optionally, the wand 17 may not be used. Instead, the RF transmitter may be positioned within the programmer 12a. In such an embodiment, the programmer 12a is positioned within close proximity to the IMD 10 in order to wake the IMD 10 up to establish a communication link therebetween. For example, the programmer 12a may be a handheld device, such as a tablet, cellular/smart phone, laptop computer, and/or the like.

Figure 2:
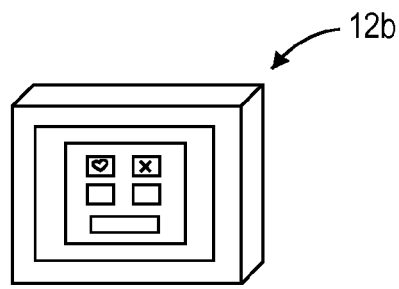
FIG. 2 illustrates a front view of a programmer, according to an embodiment of the present disclosure.

FIG. 2 illustrates an isometric front view of a programmer 12b, according to an embodiment of the present disclosure. The programmer 12b may be used in place of the programmer 12a shown in FIG. 1. The programmer 12b may be a handheld device, for example, a cellular or smart phone, such as an iPhone, a tablet device (for example, a Kindle or iPad), and the like.

Figure 3:
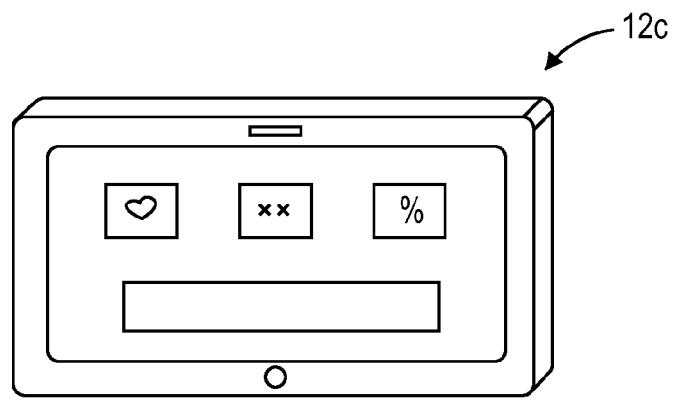
FIG. 3 illustrates an isometric front view of a programmer, according to an embodiment of the present disclosure.

FIG. 3 illustrates an isometric front view of a programmer 12c, according to an embodiment of the present disclosure. The programmer 12c may be used in place of the programmer 12a shown in FIG. 1. The programmer 12c may be a handheld device, for example, a tablet, such as an iPad.

Figure 4:
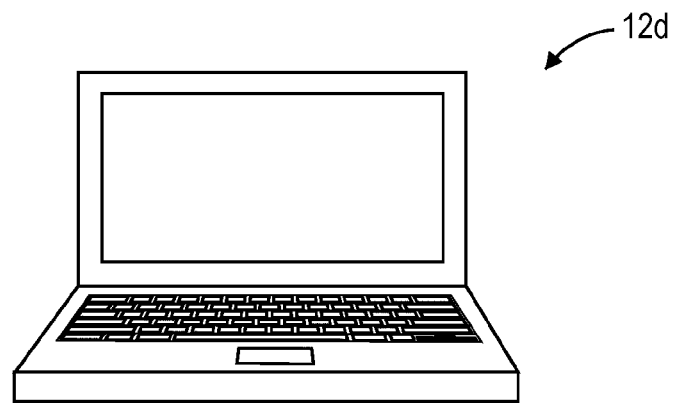
FIG. 4 illustrates an isometric front view of a programmer, according to an embodiment of the present disclosure.

FIG. 4 illustrates an isometric front view of a programmer 12d, according to an embodiment of the present disclosure. The programmer 12d may be used in place of the programmer 12a shown in FIG. 1. The programmer 12d may be a laptop computer, for example.

Referring to FIGS. 1-4, any of the programmers 12b-12d may be used in place of the programmer 12a, and each may include an RE transmitter that may be used to wake up the IMD 10, when positioned within close proximity of the IMD 10, such as within 0-1 meter. As such, the separate and distinct wand 17 shown in FIG. 1 may not be used, as its functionality may be incorporated directly into any of the programmers 12a-12d.

Figure 5:
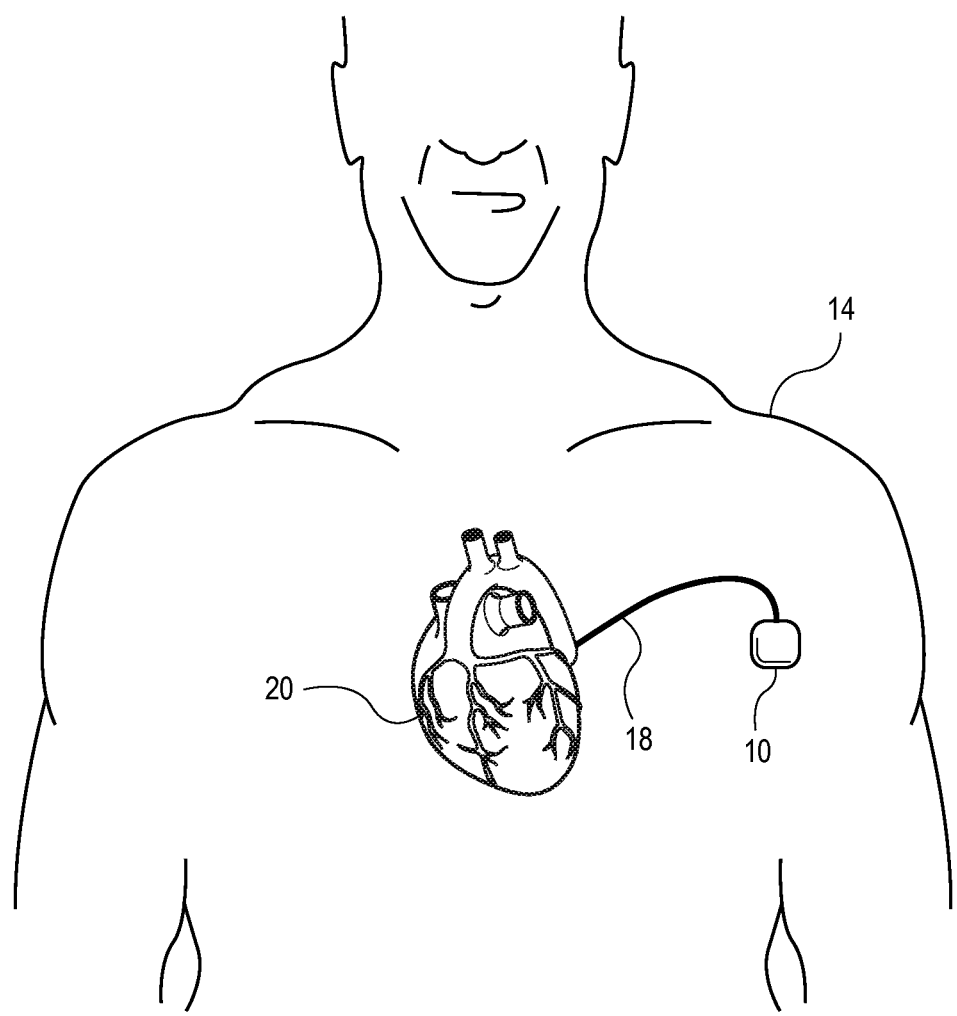
FIG. 5 illustrates an IMD implanted in a patient, according to an embodiment of the present disclosure.

FIG. 5 illustrates the IMD 10 implanted in the patient 14, according to an embodiment of the present disclosure. The IMD 10 may be an implantable pacemaker, for example. One or more leads 18 provide a patient connection interface that connects the IMD 10 to the heart 20, for example. The IMD 10 may provide therapy, such as stimulation of the heart 20 and rhythm control, through the lead(s) 18. In order to transmit and receive RF signals, the IMD 10 may include a transceiver and/or an antenna.

Figure 6:
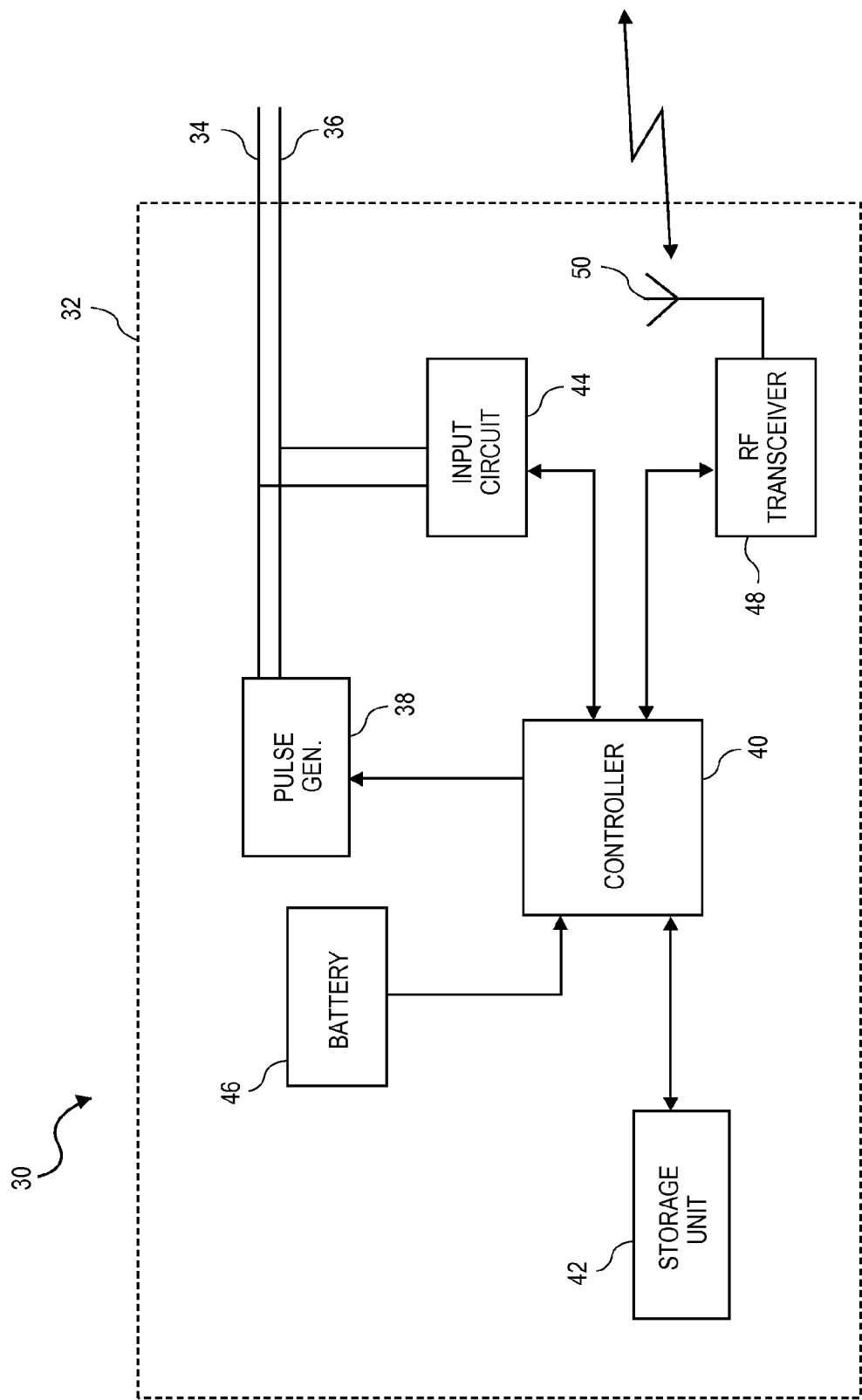
FIG. 6 illustrates a functional block diagram of an IMD, according to an embodiment of the present disclosure.

FIG. 6 illustrates a functional block diagram of an IMD 30, according to an embodiment of the present disclosure. The IMD 30 may be a bi-ventricular pacemaker, for example. The IMD 30 may include a housing 32 that is hermetically sealed and biologically inert. The housing 32 may be conductive and may thus serve as an electrode. The IMD 30 may be connectable to one or more leads, such as a ventricular lead 34 that is configured to be implanted in a right ventricle of the heart and an atrial lead 36 that is configured to be implanted in a right atrium of the heart. The leads 34 and 36 may include one or more electrodes, such as a tip electrode or a ring electrode that may be configured to measure impedance or transmit pacing pulses for causing depolarization of cardiac tissue adjacent to the electrodes generated by a pace pulse generator 38 under influence of a controller or controlling circuit 40 that may include a microprocessor. The controller 40 is configured to control parameters, such as pace pulse parameters. The pace pulse parameters may include output voltage and pulse duration, for example.

A memory or storage unit 42 may be connected to the controller 40. The storage unit 42 may include a random access memory (RAM), a non-volatile memory, such as a read-only memory (ROM), a scratchpad, and the like. Detected signals from the patient's heart may be processed in an input circuit 44 and forwarded to the controller 40 for use in logic timing determination. The IMD 30 may be powered by a battery 46, which supplies electrical power to all active electrical components of the pacemaker.

The IMD 30 may include an RF module or transceiver 48 for wireless communication of signals to/from an external programmer, such as any of the programmers 12a-12d (shown in FIGS. 1-4). Medical personnel may prefer to monitor and/or adjust parameters of the IMD 30 or to perform reprogramming. The transceiver 48 may be connected to one or more antennas 50.

The RF module or transceiver 48 may be operatively connected to the antenna(s) 50 and configured to periodically listen for an RF communication request. As an example, the RF transceiver 48 may periodically, such as every two seconds, listen for an RF communication request over the first frequency band, such as the 2.45 GHz band. If the RF transceiver 48 detects a communication request from an external programmer, the RF transceiver 48 sends a signal to the controller 40, which then switches the RF transceiver 48 from the first frequency band to the second frequency band, such as an MICS band, in order to communicate with the external programmer. Before or after the RF transceiver 48 switches to the second frequency band, the controller 40, through the RF transceiver 48, transmits a response signal to the external programmer, which receives the response signal and acknowledges that the IMD 30 is communicating with the external programmer. As such, the external programmer may wake the IMD 30 up through a communication request or signal at the first frequency band. The external programmer may wake the IMD 30 up when positioned in close proximity with the IMD 30. Optionally, a separate and distinct wand may be placed in close proximity with the IMD 30 in order to wake the IMD 30 up so that a communication link may be established between the IMD 30 and the external programmer.

Figure 7:
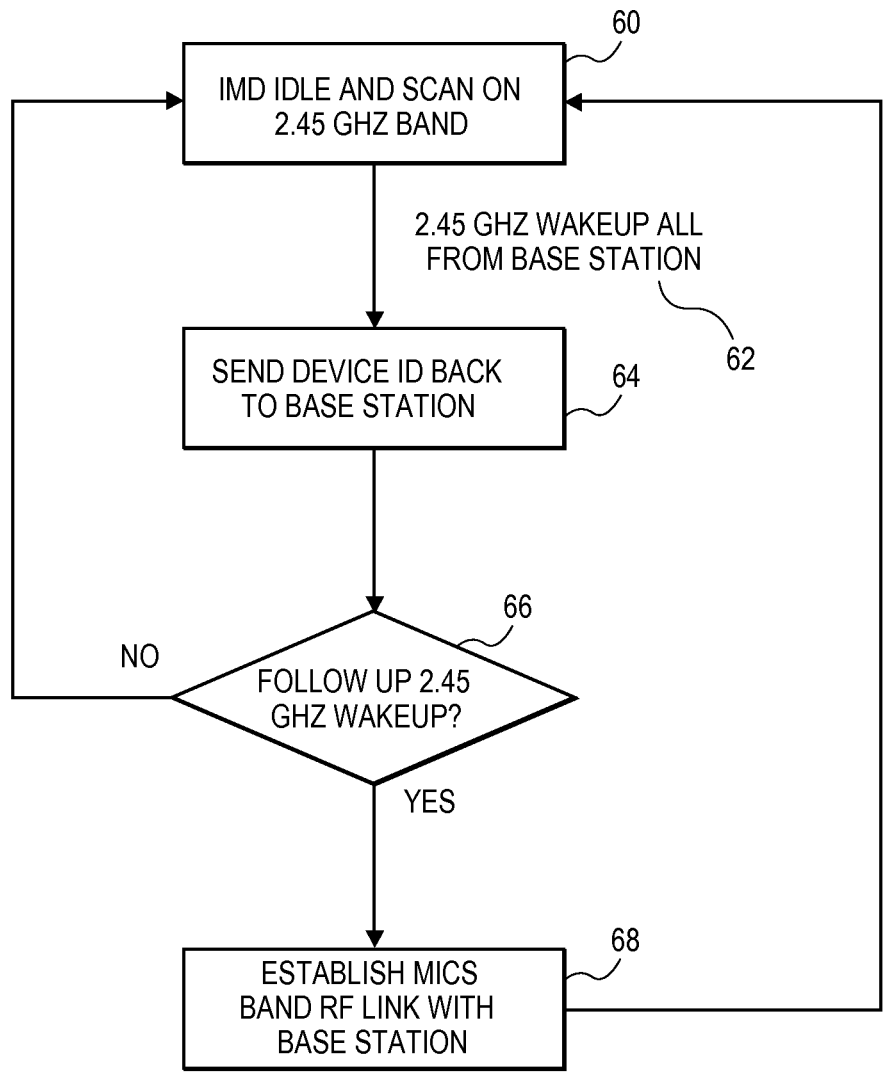
FIG. 7 illustrates a flow chart for a process of waking up an IMD, according to an embodiment of the present disclosure.

FIG. 7 illustrates a flow chart for a process of waking up an IMD, according to an embodiment of the present disclosure. The process begins at 60, in which the IMD, such as the IMD 30 (shown in FIG. 6), is idle and scans for a communication request over a 2.45 GHz band. At 62, the external programmer sends a wakeup call to the IMD. The IMD receives the wakeup call from the external programmer over the 2.45 GHz band. Then, at 64, the IMD transmits its identification data, such as an identification or serial number, back to the external programmer or base station. At 66, one or both of the IMD and the external programmer determine if additional communication or a follow-up communication should occur between the external programmer and the IMD. If not, the process returns to 60. If, however, further communication is to be established, the process continues to 68, in which communication over the MICS band is established between the IMD and the external programmer. Once the communication over the MICS band is complete, the process returns to 60.

Figure 8:
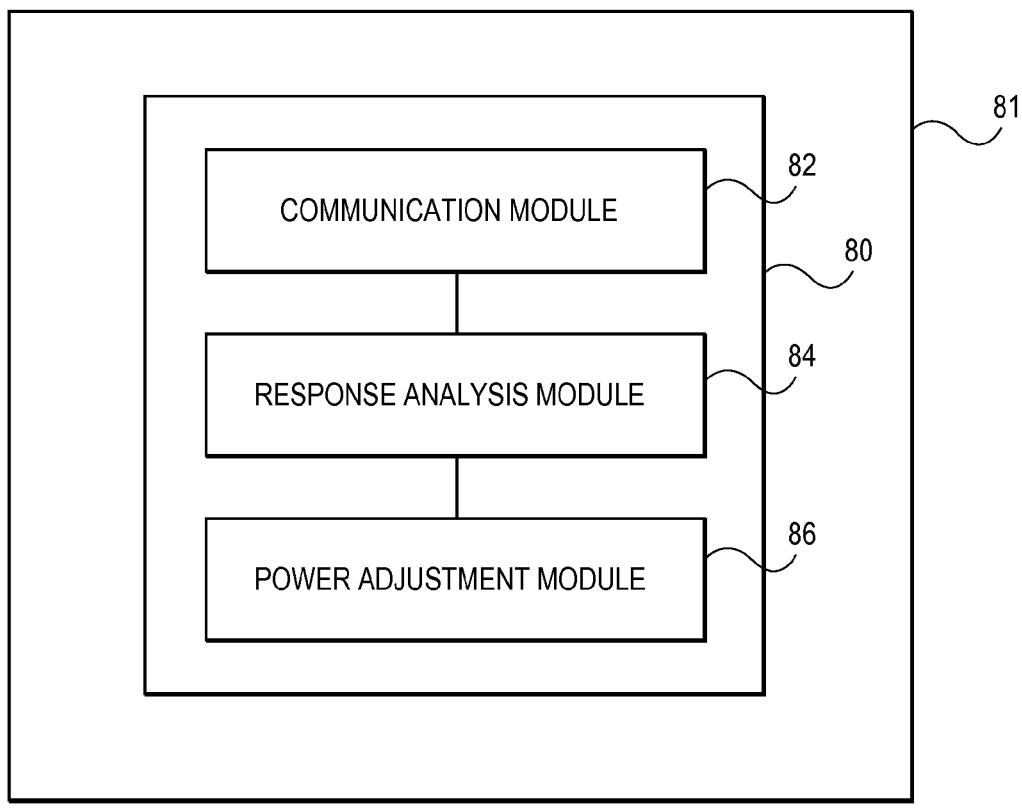
FIG. 8 illustrates a functional block diagram of a device communicator, according to an embodiment of the present disclosure.

FIG. 8 illustrates a functional block diagram of a device communicator 80, according to an embodiment of the present disclosure. The device communicator 80 may be housed within an external programmer 81, such as any of the programmers 12a-12d, shown in FIGS. 1-4, for example, or an external instrument, such as a portable device, such as an iPhone, iPad, or the like. For example, the device communicator 80 may be an integrated chip housed within the external programmer 81. The device communicator 80 is configured to communicate with one or more IMDs. Alternatively, the device communicator 80 may be housed within a wand, such as the wand 17, shown in FIG. 1.

The device communicator 80 may include a communication module 82 operatively connected to a response analysis module 84, which is, in turn, operatively connected to a power adjustment module 86. The communication module 82 may be configured to communicate with an IMD through RF signals. The communication module 82 may include one or more antennas and transceivers that are configured to communicate with an IMD and, optionally, a wand, such as shown in FIG. 1. The device communicator 80 may be within the external programmer 81. Alternatively, the device communicator 80 may be within a wand that is configured to communicate with the external programmer 81.

In operation, the external programmer 81 sends a communication request or signal to an IMD through the communication module 82. If a separate wand is used, the wand is positioned in close proximity to the IMD in order to wake the IMD up, so that a communication link may be established with the external programmer 81. Optionally, the external programmer 81 itself may be positioned within close proximity to the IMD in order to wake the IMD up and communicate therewith. In both cases, an RF communication signal may be transmitted from the external programmer 81, and when either the wand or the external programmer 81 itself is positioned within close proximity to the IMD (such as within 1 meter or less), the IMD detects the communication request (such as through an integral RF chip), and wakes up by switching to the second frequency band, at which point the IMD sends a response signal back to the external programmer 81.

The response analysis module 84 receives the response signal from the IMD by way of the communication module 82. The response analysis module 84 analyzes the response signal to determine whether a communication link has been established with the IMD. For example, the response analysis module 84 may recognize the IMD through a response signal that includes a device identifier, such as a serial number, for example. If the response analysis module 84 detects only a single IMD communicating with the external programmer 81, the response analysis module 84 may send a confirmation signal back to the communication module 82, which then allows for communication between the IMD and the external programmer 81 over the second frequency band, such as an MICS band.

If, however, the response analysis module 84 detects multiple IMDs communicating with the external programmer 81, the response analysis module 84 sends a power-adjustment request signal to the power adjustment module 86. The power-adjustment request signal may include the number of IMDs communicating with the external programmer 81. The power adjustment module 86 receives the power-adjustment request signal and adjusts the transmission power for a transmission request that is used to transmit a message over the frequency band, whether the first or second frequency band, over which communication with the multiple IMDs is occurring. The power adjustment module 86 reduces the transmission power for the transmission request that is used to transmit a message over the frequency band by a predetermined, incremental amount. At the lower power frequency band, the response analysis module 84 then listens for response signals from the IMDs. When only one response signal from a signal IMD is received, the response analysis module sends a confirmation signal back to the communication module 82, which then allows for communication between the single IMD and the external programmer 81. If, however, multiple IMDs are still communicating with the external programmer 81, the response analysis module 84 sends another power-adjustment request signal to the power adjustment module 86, which then reduces the power of the transmission request over the frequency band. The process repeats until only a single IMD is in communication with the external programmer 81.

Because the power of the transmission request over the frequency band is incrementally reduced until a single IMD is in communication with the external programmer 81, the device communicator 80 ensures that the IMD (namely, the target IMD, which is the IMD of interest to a particular individual) that is in closest proximity to the external programmer 81 or wand is the IMD that communicates with the external programmer 81. That is, the transmission power for a transmission request that is used to transmit a message over the frequency band is incrementally reduced so that outlying IMDs are out of range of the frequency band. Moreover, the external programmer 81 communicates with the target IMD at a frequency band transmission power that is low, which conserves energy. Indeed, even after the device communicator 80 establishes communication with only one IMD, the device communicator 80 may continue to incrementally reduce the power until the IMD is no longer in communication with the external programmer 81. When communication with the target IMD has been cut, the power adjustment module 86 may then incrementally increase the power of the transmission request over the frequency band until the communication link with the single IMD has been re-established. In this manner, the device communicator 80 may communicate with the IMD over the frequency band at the lowest effective transmission power, thereby conserving energy.

Moreover, if the external programmer 81 attempts to establish a communication link with an IMD, but no response signals are received by the response analysis module 84, the power adjustment module 86 may incrementally increase the transmission power for the transmission request over the frequency band, until a single IMD is in communication with the external programmer 81. In terms of power adjustment, whether increases or decreases, the power adjustment module 86 may incrementally adjust the power based on predetermined percentages. For example, the incremental power adjustments may be anywhere between 0.1%-5%, for example. However, the incremental adjustments may be more or less than 0.1-5%.

Additionally, the incremental adjustments may increase or decrease based on whether or not a single IMD is in communication with the external programmer 81. For example, if the response analysis module 84 of the device communicator 80 detects response signals from three IMDs, the power adjustment module 86 may decrease the power of the transmission request over the frequency band by 5%, for example. If, after the power adjustment, the response analysis module 84 still detects response signals from three IMDs, the power adjustment module 86 may decrease the power of the transmission request over the frequency band by an additional 5%, or even 10%, for example. The process may be an iterative process that continues until one IMD is in communication with the external programmer 81. The power adjustments may incrementally increase/decrease based on the responses received. For example, a first power adjustment may be X %, while a second power adjustment may be 2X %, a third power adjustment may be 3X %, and so on. Alternatively, a first power adjustment may be X %, while a second power adjustment may be X+Y %, a third power adjustment may be X+Y+Z %, and so on. Optionally, each power adjustment may be the same percentage increase or decrease. It is to be understood that the examples of power adjustments, such as 5%, are mere examples. The power adjustment module 86 may be programmed to particular desired power adjustments, which may be more or less than 5%, for example.

In general, the device communicator adaptively adjusts the power level of the frequency band until the external device is in communication with just the target IMD, which may be the closest IMD to the external device, such as the programmer 81. The power adjustment module 86 adaptively adjusts the transmission power for the transmission request over the frequency band so as to adaptively adjust the range of the frequency band in order to encompass just the target IMD.

Once the device communicator 80 establishes a communication link with only one IMD over the frequency band at a particular power (which dictates the range of the frequency band), the IMD may switch to the second frequency band in order to communicate with the external programmer 81. Once the communication session has completed, the IMD returns to a dormant communication state such that it returns to the first frequency band in which it periodically listens for a communication request from the external programmer. Further, after the power level of the frequency band that encompasses only the target IMD has been established, when a subsequent wake-up is initiated, the device communicator 80 may initially transmit a communication request over the frequency band at the previously-established transmission power, which previously encompassed only the target IMD.

Each module 82, 84, and 86 may include one or more control units, such as processing devices that may include one or more microprocessors, microcontrollers, integrated circuits, memory, such as read-only and/or random access memory, and the like. The modules 82, 84, and 86 may be integrated into a single module and contained within a single device, such as a single integrated chip, for example. Alternatively, each module 82, 84, and 86, may be its own separate and distinct module, and contained within a respective integrated chip, for example.

One or more of the modules 82, 84, and 86 may include any suitable computer-readable media used for data storage. For example, one or more of the modules 82, 84, and 86 may include computer-readable media. The computer-readable media are configured to store information that may be interpreted by the modules 82, 84, and 86. The information may be data or may take the form of computer-executable instructions, such as software applications, that cause a microprocessor or other such control unit within the modules 82, 84, and 86 to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Figure 9:
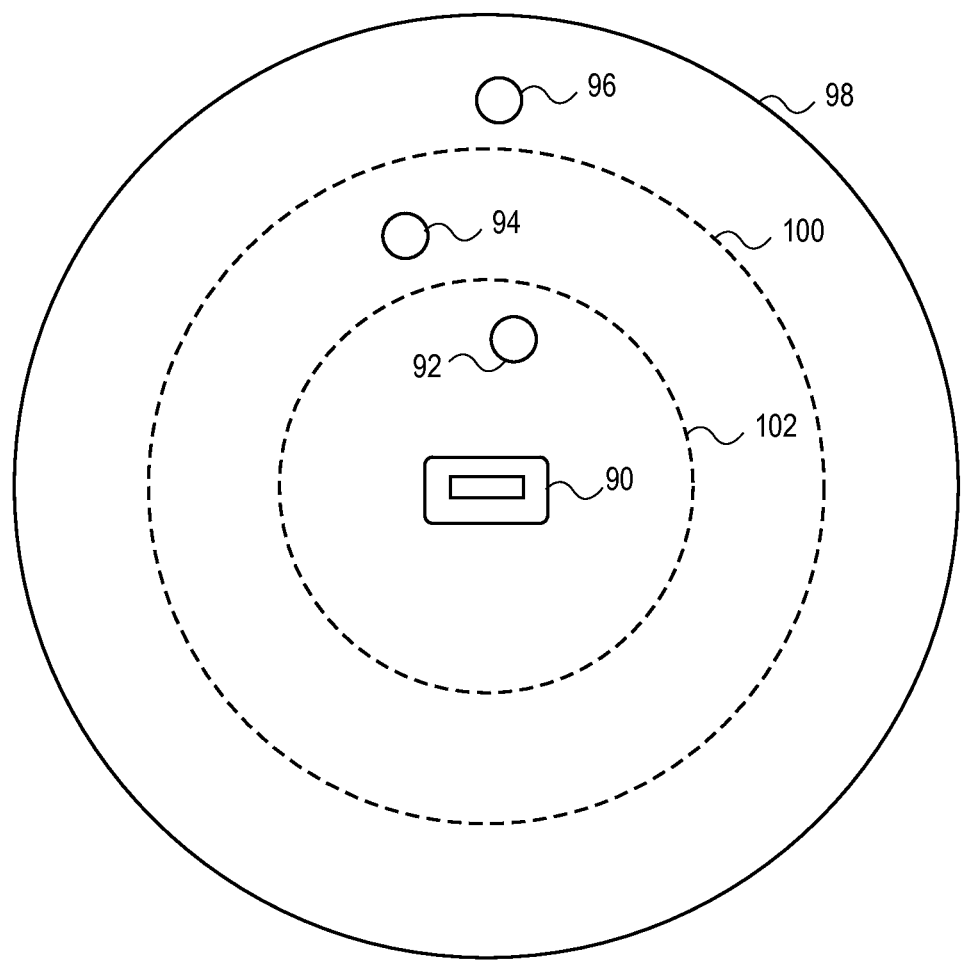
FIG. 9 illustrates a simplified diagram of an external programmer in relation to multiple IMDs, according to an embodiment of the present disclosure.

FIG. 9 illustrates a simplified diagram of an external programmer 90 in relation to multiple IMDs 92, 94, and 96, according to an embodiment of the present disclosure. The external programmer 90 may be any of those described above. The external programmer 90 includes a device communicator 80, as shown in FIG. 8. The external programmer 90 may establish a communication link with one or more of the IMDs 92, 94, and 96 when positioned in close proximity thereto. Optionally, the external programmer 90 may be in communication with a wand, such as the wand 17, which is configured to wake up the IMDs 92, 94 and 96 when positioned in close proximity thereto. Again, close proximity may be 1 meter or less. Optionally, the close proximity may be substantially less than 1 meter. For example, the close proximity may be less than 5 centimeters.

Referring to FIGS. 8 and 9, initially, the external programmer 90 transmits a communication request, over a select frequency band, at a first power that has an extended range 98 that encompasses all three of the IMDs 92, 94, and 96. For example, the first power may represent a predetermined long-range power level intended to reach IMDS that are a predetermined range from the external programmer 90. As such, the external programmer 90 receives response signals from all three IMDs 92, 94, and 96. For example, through the communication module 82, the response signal analysis module 84 receives response signals from all three IMDs 92, 94, and 96. In response, the response analysis module 84 sends a power-adjustment request signal to the power adjustment module 86 requesting that the transmit power, at which communication requests are transmitted over the frequency band, be reduced as there are too many IMDs 92, 94 and 96 within extended range associated with the initial transmit power. Accordingly, the power adjustment module 86 reduces the transmission power for a transmission request over the frequency band so that the range 100 of the frequency band is reduced. However, the response signal analysis module 84 still detects the presence of the IMDs 92 and 94, as both are within the range 100. Therefore, the response signal analysis module 84 sends another power-adjustment request signal to the power adjustment module 86 instructing the power adjustment module 86 to further reduce the transmission power for a transmission request over the frequency band. The power adjustment module 86 then reduces the power of the transmission request over the frequency band again so that the range 102 of the frequency band is further reduced. Only the IMD 92 is within the range 102. The response signal analysis module 84 detects the presence of the IMD 92 within the range 102, and therefore sends a signal to the external programmer 90 to continue communication with the IMD 92.

Alternatively, the power adjustment module 86 may continue to reduce the power of the transmission request over the frequency band so that the IMD 92 is out of range. When no IMDs are detected, the power adjustment module 86 may then increase the power of the transmission request over the frequency band so that it just encompasses the IMD 92. In this manner, the power adjustment module 86 may ensure that the external programmer 90 uses a minimal amount of power to communicate with the IMD 92.

Figure 10:
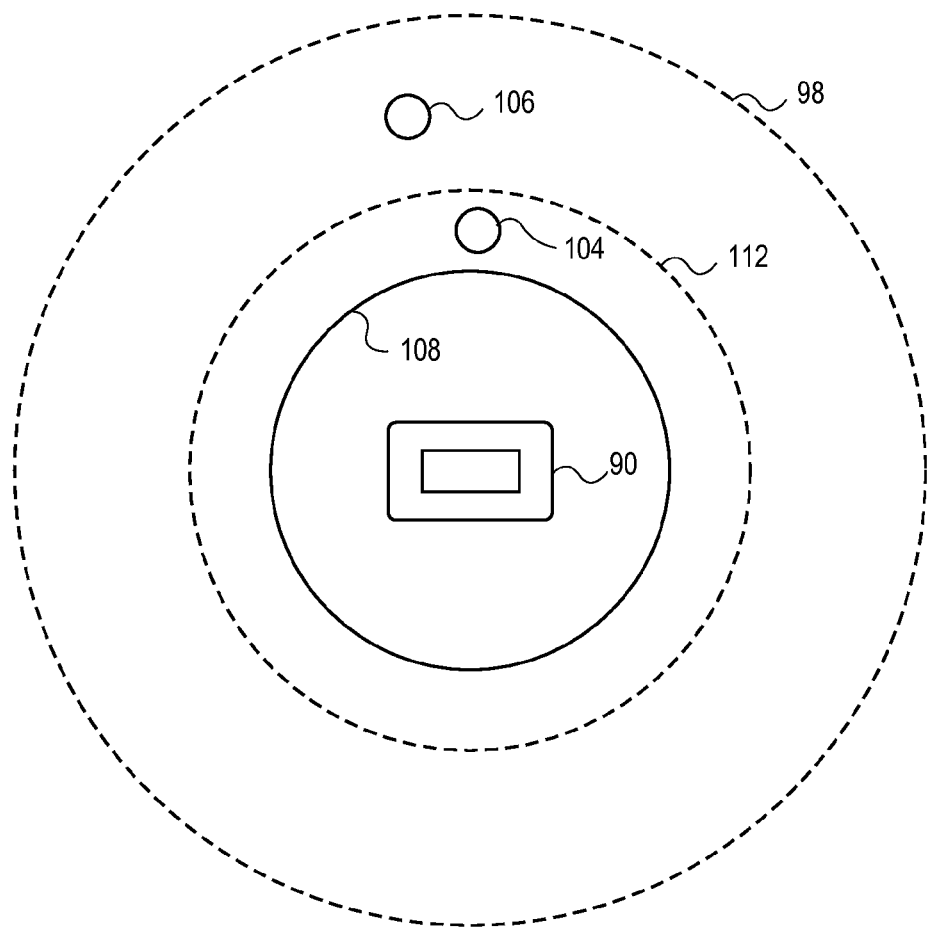
FIG. 10 illustrates a simplified diagram of an external programmer in relation to multiple IMDs, according to an embodiment of the present disclosure.

FIG. 10 illustrates a simplified diagram of the external programmer 90 in relation to multiple IMDs 104 and 106, according to an embodiment of the present disclosure. Referring to FIGS. 8 and 10, initially, the IMD 90 transmits a communication request over a frequency band at a first power that produces a first range 108. However, the response signal analysis module 84 detects no response signals from any of the IMDs 104 and 106. As such, the response signal analysis module 84 sends a power-adjustment request signal to the power adjustment module 86 to increase the power of the transmission request over the frequency band so that the range 110 of the frequency band is increased. At the increased range 110, the response analysis module 84 receives response signals from both the IMDs 104 and 106. Consequently, the response analysis module 84 sends a power-adjustment request signal to the power adjustment module 86 to reduce the power of the transmission request over the frequency band to a range 112 that is less than the range 110, but more than the range 108. Only the IMD 104 is within the range 112. The response signal analysis module 84 detects the presence of the IMD 104 within the range 112, and therefore sends a signal to the external programmer 90 to continue communication with the IMD 112.

Figure 11:
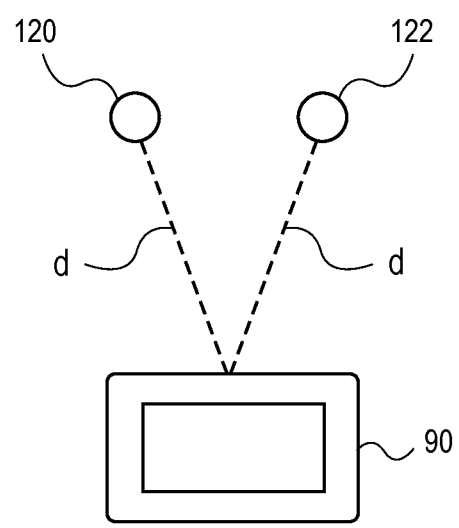
FIG. 11 illustrates a simplified diagram of an external programmer that is equidistant from two IMDs, according to an embodiment of the present disclosure.

FIG. 11 illustrates a simplified diagram of the external programmer 90 that is equidistant from two IMDs 120 and 122, according to an embodiment of the present disclosure. As shown in FIG. 11, the programmer 90 is a range d from each IMD 120 and 122. The range is a function of distance, intervening structures, other RF activity, interference, and the like. For example, if a clear path exists between the IMDs 120 and 122 and the programmer 90, the range will be a first distance. If, however, there are intervening structures, other RF activity, or interference therebetween, the range will be a second distance that is less than the first distance. Thus, even if the range is constant, the distance may be reduced if intervening structures, other RF activity, or interference occur between the IMDs 120 and 122 and the programmer 90. Referring to FIGS. 8 and 11, the device communicator 80 may continually adjust the power of the transmission request over the frequency band in an effort to receive only a response signal from one of the IMDs 120 and 122. After a predetermined amount of time, however, if multiple response signals continue to be received, the response analysis module 84 may send a signal to the external programmer to display a message on a display of the external programmer instructing an individual to move the external programmer 90 closer to the target IMD 120 or 122. As the external programmer 90 is moved closer to the IMD 120 or 122, the relative ranges change so that the target IMD 120 or 122 is not the same range to the external programmer 90 as the other IMD 120 or 122. Therefore, the power adjustment process may continue as described above with respect to FIG. 9, for example.

As described above, embodiments of the present disclosure provide a system and method for waking up the closest IMD to the external programmer and/or wand. Embodiments of the present disclosure provide a system and method for selectively waking up a target IMD among a plurality of IMDs.

Embodiments of the present disclosure may be configured to wake up a target IMD over a 2.45 GHz frequency band, and then establish the MICS band with the target IMD. By adjusting the power of the transmission request over the frequency band, the embodiments of the present disclosure allow an external programmer to wake up the closest IMD, which is the target IMD.

Figure 12:
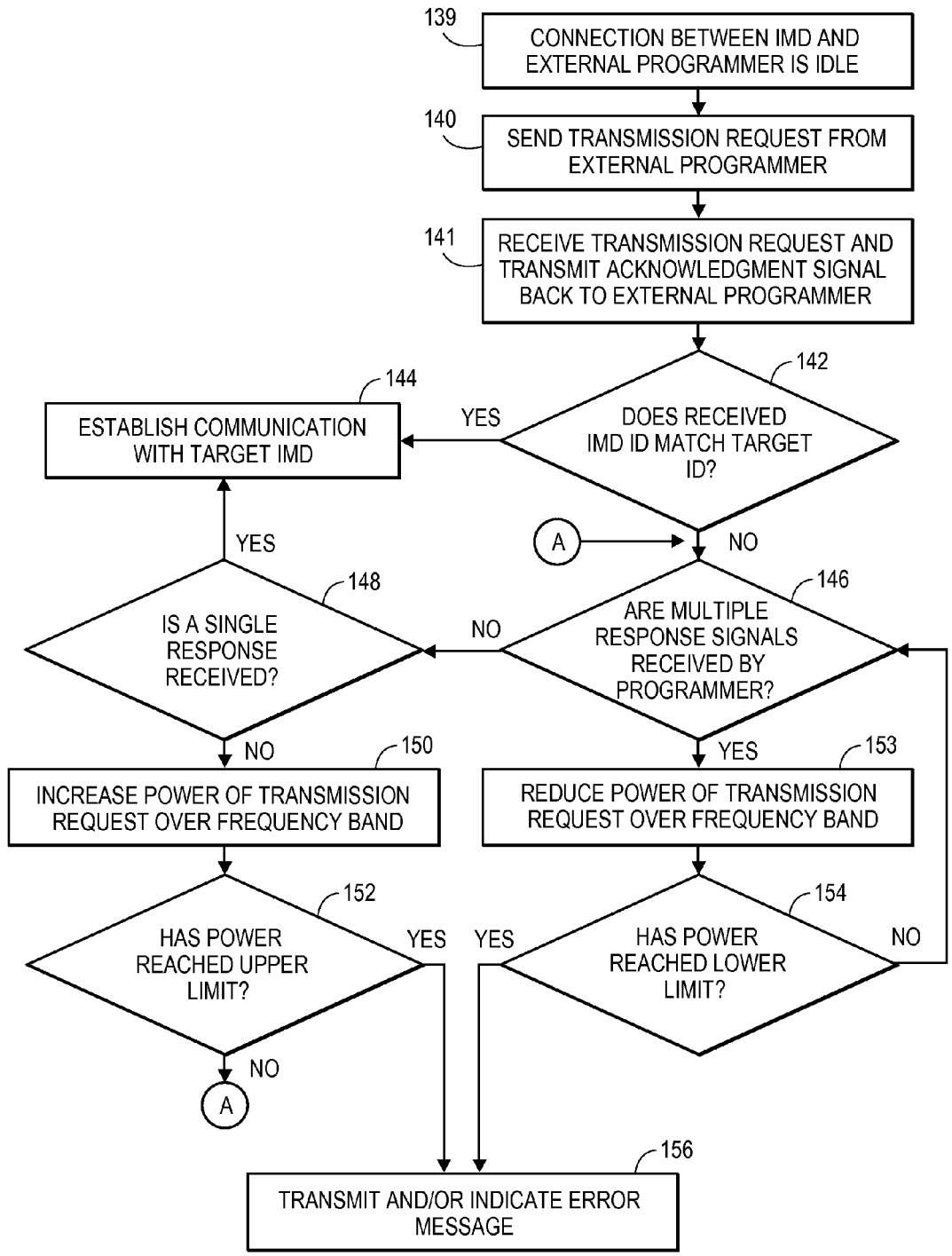
FIG. 12 illustrates a flow chart of a method of selectively communicating with a target IMD, according to an embodiment of the present disclosure.

FIG. 12 illustrates a flow chart of a method of selectively communicating with a target IMD, according to an embodiment of the present disclosure. The method begins at 139, in which a connection between an external programmer and one or more IMDs is idle. At 140, a communication or transmission request is broadcast from an external programmer over a first frequency band, such as a 2.45 GHz band. The transmission request may be a wake up broadcast that is received by any IMDs within a range of the broadcast. After sending the broadcast, the external programmer may wait a predetermined time, such as 2.5 seconds, to determine whether any acknowledgement or response signals are transmitted back to the external programmer. A default wakeup setting may be set by the external programmer and/or the IMD at the first frequency band. For example, the IMD may be programmed to wake up and send an acknowledgement signal to the external programmer when it receives a particular communication request.

At 141, an IMD within range of the broadcasted transmission request from the external programmer receives the transmission request and transmits an acknowledgement signal back to the external programmer. The acknowledgement signal may include identification information of the IMD. At 142, it is determined whether the identification of the IMD is known. For example, the external programmer determines whether the IMD that has transmitted the acknowledgement signal is the target IMD. The external programmer determines whether the received identification information of the IMD matches stored target IMD identification information. For example, the external programmer may store data related to the IMD serial number or other such identifying information that is specific to the target IMD. When the IMD transmits an acknowledgement or response signal back to the external programmer, the specific identification data of the IMD may be included in the acknowledgement or response signal, and the external programmer may match the identification data with the stored data and then establish communication with the target IMD at 144.

As noted above, the IMD may include an RF receiver that periodically listens for an RF wakeup call transmitted from the external programmer, as shown in FIG. 7. For example, the IMD may include an RF receiver that listens for a wakeup call on a first frequency band, such as a low power, high frequency band (for example, a 2.45 GHz band). As an example, the IMD may listen for the wakeup call every 1 or 2 seconds. The external programmer may transmit the wakeup call over the first frequency band. When the external programmer or an RF wand is positioned within close proximity to the IMD, a communication link may be established between the IMD and the external programmer, which may then communicate over a second frequency band, such as a high power, low frequency band (for example, an MICS band in the range of 402-405 MHz).

The external programmer may adjust the transmission power for a predetermined period of time within which communication with a single IMD may be established. For example, the predetermined period of time may be between 1 and 5 seconds. However, the predetermined period of time may be shorter or longer than 1 and 5 seconds. If communication is not established with a single IMD within the predetermined period of time, the response analysis module of the device communicator may transmit an error signal to the external programmer to display an appropriate error message.

Returning to 142, if the IMD identification is unknown, the method continues to 146, in which it is determined whether multiple response signals from multiple IMDs are received by the external programmer. For example, if the received IMD identification and the stored IMD identification do not match at the programmer, the method continues to 146. If, at 146, the external programmer does not receive multiple response signals, the method continues to 148, in which it is determined whether a single response signal is received by the external programmer. If, at 148, the external programmer receives only one response signal from one IMD, the method continues to 144, in which the external programmer communicates with the target IMD. If, however, at 148 there is no response signal received by the external programmer, the method continues to 150, in which the transmission power is incrementally increased. At 152, the external programmer determines if the transmission power has reached an upper limit, past which the external programmer is unable to increase power. If the upper limit has been reached, the method continues to 153, in which the external programmer transmits or indicates an error message, such as to suggest replacement of the programmer, for example. If, however, the upper power limit has not been reached, the method returns to 146.

If, at 146, there are multiple acknowledgement or response signals received by the external programmer, the method continues to 153, in which the transmission power is reduced. At 154, the external programmer determines whether the transmission power has reached a lower limit. For example, the lower limit may be a transmission power that is incapable of establishing communication with an IMD. If the lower power limit has been reached at 154, the method continues to 156, in which an error message is transmitted or indicated at the external programmer. For example, the error message may include a suggestion to replace the external programmer.

If, however, the lower power limit has not been reached at 154, the method then returns to 146. For example, if the external programmer receives five acknowledgement or response signals from five respective IMDs, the external programmer decreases the transmission power, as the external programmer is attempting to communicate with a single IMD, but not multiple IMDs.

The external device, such as a programmer, is configured to adjust the power of the transmission request over the frequency band, such as the first frequency band, until a single IMD is in communication with the external programmer. If, as noted above, the external programmer continues to adjust the power of the transmission request over the frequency band but no response signals are received or too many response signals from multiple IMDs are received for a predetermined period of time, the response analysis module of the device communicator may send a signal to the external programmer to display an error message. Alternatively, a replacement message may be displayed, in which the external programmer may suggest a replacement wand or replacement device communicator.

A power setting of the external programmer may be initially set at a maximum or minimum power, and then adjusted down or up, as shown in FIG. 12. If initially set to a maximum power, for example, the power level of the external programmer may not be adjusted up therefrom. Similarly, if initially set to a minimum power, the power level of the external programmer may not be adjusted down therefrom.

Figure 13:
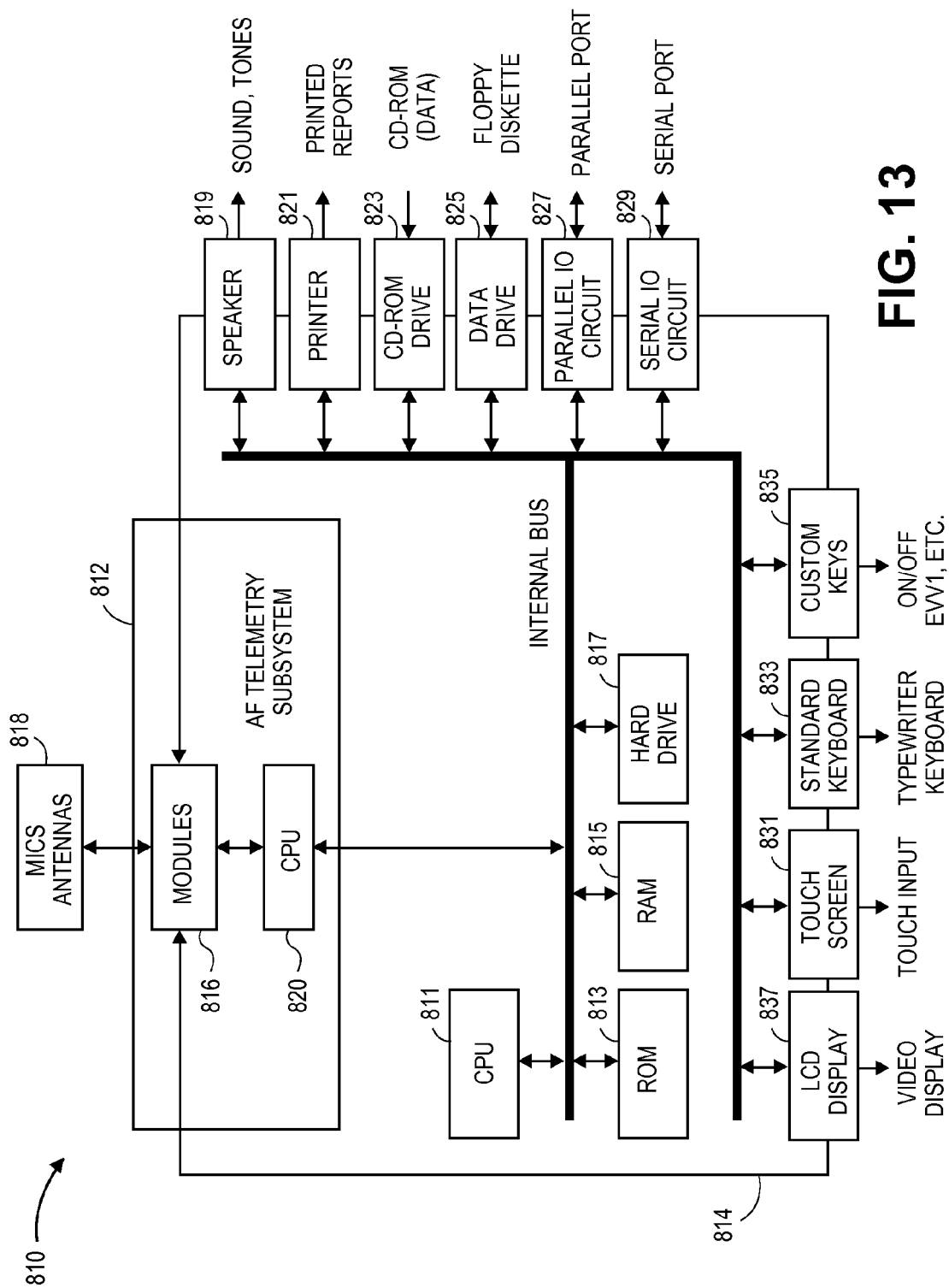
FIG. 13 illustrates a functional block diagram of an external device, according to an embodiment of the present disclosure.

FIG. 13 illustrates a functional block diagram of an external device, such as a programmer 810, according to an embodiment of the present disclosure. The programmer 810 may represent a handheld portable tablet-type programmer device used by physicians and others to communicate with, collect data from, program and reprogram, an IMD. Alternatively, the programmer 810 may be a cell phone, personal computer, or laptop computer. Additionally, the programmer 810 may be a standalone antenna assembly. Optionally, the programmer 810 may be a patient care system, such as the Merlin® home patient care system offered by St. Jude Medical. The programmer 810 may include a device communicator 812 that communicates with an implantable medical device (IMD) and/or a network 814. The device communicator 812 may be similar to the device communicator 80, described above. The device communicator 812 may include modules 816 (such as the modules 82, 84, and 86 described with respect to FIG. 8) operatively connected to one or more MICS antennas 818. The modules 816 may also be operatively connected to a controller or processing unit 820. Alternatively, at least a portion of the device communicator 812, such as a communications module, may be contained within a wand, such as the wan 17 shown in FIG. 1.

The programmer 810 may be a workstation, a portable computer, an IMD programmer, a PDA, a cell phone and the like. The programmer 810 may include an internal bus that connects/interfaces with a Central Processing Unit (CPU) 811, ROM 813, RAM 815, a hard drive 817, speaker 819, a printer 821, a CD-ROM drive 823, a data drive 825, a parallel I/O circuit 827, a serial I/O circuit 829, a display 837, a touch screen 831, a standard keyboard connection 833, custom keys 835, and the device communicator 812. The internal bus may include an address/data bus that transfers information between the various components described herein. The hard drive 817 may store operational programs as well as data, such as waveform templates and detection thresholds.

The CPU 811 may include a microprocessor, a microcontroller, or equivalent control circuitry, designed specifically to control interfacing with the programmer 810 and with the IMD or network 814. The CPU 811 may include RAM or ROM memory, logic and timing circuitry, state machine circuitry, and I/O circuitry to interface with the IMD. The touch screen 831 may display graphic information relating to the IMD and/or the network 814. The touch screen 831 is configured to accept a user's touch input when selections are made. The keyboard 833 (for example, a "QWERTY" typewriter keyboard) is configured to allow a user to enter data into the displayed fields, as well as interface with the RF telemetry subsystem 812. Further, the custom keys 835 are configured to selectively turn on/off (for example, EVVI) the programmer 810. The printer 821 is configured to print copies of reports for a physician to review or to be placed in a patient file, and the speaker 819 is configured to provide an audible warning (for example, sounds and tones) to the user. The parallel I/O circuit 827 interfaces with a parallel port. The serial I/O circuit 829 interfaces with a serial port. The data drive 825 is configured to accept data disks, for example. Optionally, the data drive 825 may be a USB port or other interface capable of communicating with a USB device such as a memory stick. The CD-ROM drive 823 accepts CD ROMs.

As noted above, the device communicator 812 may include the central processing unit (CPU) 820 in electrical communication with the modules 816. Cardiac signals sensed by the leads may be collected by an IMD and then wirelessly transmitted to the device communicator 812 of the programmer 810.

Figure 14:
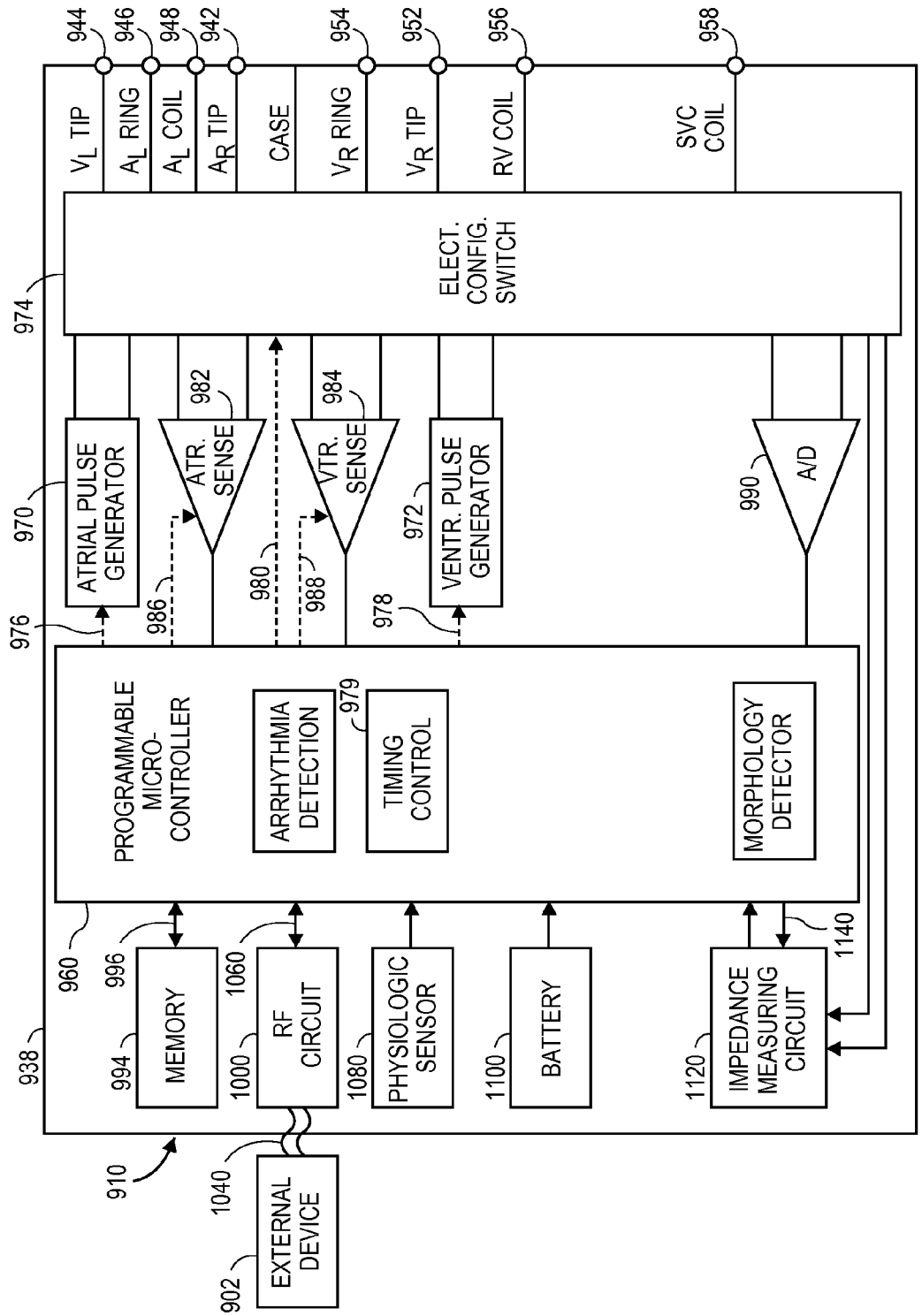
FIG. 14 illustrates a block diagram of exemplary internal components of an IMD, according to an embodiment of the present disclosure.

FIG. 14 illustrates a block diagram of exemplary internal components of an IMD 910, according to an embodiment of the present disclosure. It is to be noted that the IMD 910 is but one example of an IMD that may be used with embodiments of the present disclosure. Various other IMDs may be used in place of the IMD 910. The IMD 910 is for illustration purposes only, and it is understood that the circuitry could be duplicated, eliminated or disabled in any desired combination to provide a device capable of treating patient anatomy with cardioversion, defibrillation and/or pacing stimulation as well as providing for apnea detection and therapy. The IMD 910 includes a housing 938, which is shown schematically in FIG. 14. The housing 938 is often referred to as the "can", "case" or "case electrode" and may be programmably selected to act as the return electrode for all "unipolar" modes. The housing 938 may further be used as a return electrode alone or in combination with one or more of the coil electrodes for shocking purposes. The housing 938 further includes a connector (not shown) having a plurality of terminals, 942, 952, 954, 956 and 958 (shown schematically and, for convenience, the names of the electrodes to which they are connected are shown next to the terminals). A right atrial tip terminal ($A_R$ TIP) 942 is adapted for connection to an atrial tip electrode and a right atrial ring terminal may be adapted for connection to a right atrial ring electrode. A left ventricular tip terminal ($V_L$ TIP) 944, a left atrial ring terminal ($A_L$ RING) 946, and a left atrial shocking terminal ($A_L$ COIL) 948 are adapted for connection to a left ventricular ring electrode, a left atrial tip electrode, and a left atrial coil electrode, respectively. A right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958 are adapted for connection to a right ventricular tip electrode, right ventricular ring electrode, an RV coil electrode, and an SVC coil electrode, respectively.

The IMD 910 includes a programmable microcontroller 960 which controls operation. The microcontroller 960 (also referred to herein as a processor module or unit) includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by program code stored in memory. The details of the design and operation of the microcontroller 960 are not critical to the invention. Rather, any suitable microcontroller 960 may be used that carries out the functions described herein. Among other things, the microcontroller 960 receives, processes, and manages storage of digitized cardiac data sets from the various sensors and electrodes. For example, the cardiac data sets may include pressure data, heart sound data, and the like.

The IMD 910 includes an atrial pulse generator 970 and a ventricular/impedance pulse generator 972 to generate pacing stimulation pulses for delivery by the right atrial lead, the right ventricular lead, and/or the coronary sinus lead via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators 970 and 972 are controlled by the microcontroller 960 via appropriate control signals, 976 and 978, respectively, to trigger or inhibit the stimulation pulses.

The microcontroller 960 further includes timing control circuitry 979 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuit 982 and ventricular sensing circuit 984 may also be selectively coupled to the right atrial lead, coronary sinus lead, and the right ventricular lead, through the switch 974 for detecting the presence of cardiac activity in each of the four chambers of the heart. Accordingly, the atrial (ATR SENSE) and ventricular (VTR SENSE) sensing circuits 982 and 984 may include dedicated sense amplifiers, multiplexed amplifiers or shared amplifiers. The outputs of the atrial and ventricular sensing circuits, 982 and 984, are connected to the microcontroller 960 which, in turn, are able to trigger or inhibit the atrial and ventricular pulse generators 970 and 972, respectively, in a demand fashion in response to the absence or presence of cardiac activity in the appropriate chambers of the heart.

Cardiac signals are also applied to the inputs of an analog-to-digital (A/D) data acquisition system 990. The data acquisition system 990 is configured to acquire signals, convert the raw analog data into a digital signal, and store the digital IEGM signals in memory 994 for later processing and/or transmission to an external device 902, such as a programmer, as described above. The data acquisition system 990 is coupled to the right atrial lead, the coronary sinus lead, and the right ventricular lead through the switch 974 to sample cardiac signals across any combination of desired electrodes.

The microcontroller 960 is coupled to memory 994 by a suitable data/address bus 996, wherein the programmable operating parameters used by the microcontroller 960 are stored and modified, as required, in order to customize the operation of IMD 910 to suit the needs of a particular patient. The memory 994 also stores data sets (raw data, summary data, histograms, etc.), such as the IEGM data, heart sound data, pressure data, Sv02 data and the like for a desired period of time (e.g., 1 hour, 24 hours, 1 month, etc.). The memory 994 may store instructions to direct the microcontroller 960 to analyze the cardiac signals and heart sounds, identify characteristics of interest, and derive values for predetermined statistical parameters. The IEGM, pressure, and heart sound data stored in memory 994 may be selectively stored at certain time intervals, such as 5 minutes to 1 hour periodically or surrounding a particular type of arrhythmia of other irregularity in the heart cycle. For example, the memory 994 may store data for multiple non-consecutive 10 minute intervals.

The pacing and other operating parameters of the IMD 910 may be non-invasively programmed into the memory 994 through an RF circuit 1000 in RF communication with the external device 902, such as a programmer, trans-telephonic transceiver or a diagnostic system analyzer, or with a bedside monitor. The RF circuit 1000 is activated by the microcontroller 960 by a control signal 1060. The RF circuit 1000 allows physiological data to be sent to the external device 902 through an established communication link 1040.

The IMD 910 may also include an accelerometer or other physiologic sensor 1080, commonly referred to as a "rate-responsive" sensor because it is typically used to adjust pacing stimulation rate according to the exercise state of the patient. Optionally, the physiological sensor 1080 may further be used to detect changes in cardiac output, changes in the physiological condition of the heart, or changes in activity (e.g., detecting sleep and wake states) and to detect arousal from sleep. While shown as being included within IMD 910, it is to be understood that the physiologic sensor 1080 may also be external to IMD 910, yet still be implanted within or carried by the patient. A common type of rate responsive sensor is an activity sensor incorporating an accelerometer or a piezoelectric crystal, which is mounted within the housing 938 of IMD 910. The physiologic sensor 1080 may be used in conjunction with, or in place of, the position detector 965, for example.

The IMD 910 also includes a battery 1100, which provides operating power to all of the circuits shown. The IMD 910 is shown as having impedance measuring circuit 1120 which is enabled by the microcontroller 960 via a control signal 1140. Herein, impedance is primarily detected for use in evaluating ventricular end diastolic volume (EDV) but is also used to track respiration cycles. Other uses for an impedance measuring circuit include, but are not limited to, lead impedance, surveillance during the acute and chronic phases for proper lead positioning or dislodgement, detecting operable electrodes and automatically switching to an operable pair if dislodgement occurs, measuring respiration or minute ventilation; measuring thoracic impedance for determining shock thresholds; detecting when the device has been implanted, measuring stroke volume, and detecting the opening of heart valves, etc. The impedance measuring circuit 1120 is advantageously coupled to the switch 974 so that impedance at any desired electrode may be obtained.

Embodiments of the present disclosure may include RF-only IMDs and external programmers that are devoid of inductive hardware, such as telemetry coils. As described above, embodiments of the present disclosure provide systems and methods for selectively communicating with a target IMD that may be in the general vicinity of a plurality of IMDs. Embodiments of the present disclosure reduce the possibility of erroneous communication between a programmer and an IMD.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An external device comprising:
a communication module configured to communicate with a target implantable medical device (IMD) within a vicinity of other IMDs;
a response analysis module configured to receive and analyze a target response signal from the target IMD and other response signals from the other IMDs and based thereon, generate one or more power-adjustment request signals; and a power adjustment module configured to receive the one or more power-adjustment request signals from the response analysis module, wherein the power adjustment module is configured to adaptively adjust a power of a transmission request over a first frequency band based on the one or more power-adjustment request signals until the response analysis module receives only the target response signal from the target IMD, wherein the external device is configured to communicate with the target IMD over a second frequency band after the response analysis module receives only the target response signal, and wherein the power adjustment module is configured to, at least one of:
  incrementally decrease the power of transmission request over the first frequency band when the response analysis module receives one or more of the other signals from one of more the other IMDs, and
  incrementally increase the power of the transmission request over the first frequency band when the response analysis module does not receive the target response signal.

2. The external device of claim 1, wherein the external device is configured to be positioned closer to the target IMD than the other IMDs.

3. The external device of claim 1, wherein one or more of the communication module, the response analysis module, and the power adjustment module are contained within a wand that is configured to wake up the target IMD.

4. The external device of claim 1, wherein one or more of the communication module, the response analysis module, and the power adjustment module are contained within one or more of a patient home care system, a tablet, a smart phone, and a laptop computer.

5. The external device of claim 1, wherein the communication module is devoid of telemetry hardware that is configured to facilitate inductive communication.

6. The external device of claim 1, wherein the power adjustment module is configured to incrementally decrease the power of transmission request over the first frequency band when the response analysis module receives one or more of the other signals from one of more the other IMDs.

7. The external device of claim 1, wherein the power adjustment module is configured to incrementally increase the power of the transmission request over the first frequency band when the response analysis module does not receive the target response signal.

8. The external device of claim 1, wherein the first frequency band is 2.45 GHz, and wherein the second frequency band is within a range of 402-485 MHz.

9. A system, comprising:
a target Implantable medical device (IMD); and
an external device comprising:
  a communication module configured to communicate with the target IMD;
  a response analysis module configured to receive and analyze a target response signal from the target IMD and other response signals from other IMDS, and based thereon, generate one or more power-adjustment request signals; and
a power adjustment module configured to receive the one or more power-adjustment request signals from the response analysis module, wherein the power adjustment module is configured to adaptively adjust a power of a transmission request over a first frequency band based on the one or more power-adjustment request signals until the response analysis module receives only the target response signal from the target IMD, wherein the external device is configured to communicate with the target IMD over a second frequency band after the response analysis module receives only the target response signal, and wherein the power adjustment module is configured to, at least one of:
  incrementally decrease the power of the transmission request over the first frequency band when the response analysis module receives one or more of the other signals from one of more the other IMDs, and
  incrementally increase the power of the transmission request over the first frequency band when the response analysis module does not receive the target response signal.

10. The system of claim 9, wherein the target IMD is closer to the external device than the other IMDs.

11. The system of claim 9, wherein one or more of the communication module, the response analysis module, and the power adjustment module are contained within a wand that is configured to wake up the target IMD.

12. The system of claim 9, wherein one or more of the communication module, the response analysis module, and the power adjustment module are contained within one or more of a patient home care system, a tablet, a smart phone, and a laptop computer.

13. The system of claim 9, wherein each of the communication module and the target IMD is devoid of telemetry hardware that is configured to facilitate inductive communication.

14. The system of claim 9, wherein the power adjustment module is configured to incrementally decrease the power of the transmission request over the first frequency band when the response analysis module receives one or more of the other signals from one of more the other IMDs.

15. The system of claim 9, wherein the power adjustment module Is configured to incrementally increase the power of the transmission request over the first frequency band when the response analysis module does not receive the target response signal.

16. The system of claim 9, wherein the first frequency band is 2.45 GHz, and wherein the second frequency band is within a range of 402-405 MHz.

17. A method of selectively communicating with a target implantable medical device (IMD) within a vicinity of other IMDs, the method comprising:
  communicating with the target IMD with a communication module;
  receiving a target response signal from the target IMD with a response analysis module;
  receiving one or more other response signals from one or more of the other IMDs with the response analysis module;
  analyzing the target response signal and the one or more other response signals with the response analysis module and based thereon, generating one or more power-adjustment request signals;
  receiving the one or more power-adjustment request signals from the response analysis module at a power adjustment module;
  adaptively adjusting a power of a transmission request over a first frequency band based on the one or more power-adjustment request signals until the response analysis module receives only the target response signal from the target IMD; and communicating with the target IMD over a second frequency band after the response analysis module receives only the target response signal,
wherein the adaptively adjusting operation comprises, at least one of:
incrementally decreasing the power of the transmission request over the first frequency band when the response analysis module receives one or more of the other signals from one of more the other IMDs, and
incrementally increasing the power of the transmission request over the first frequency band when the response analysis module does not receive the target response signal.

18. The method of claim 17, wherein the communicating operation occurs when the external device is positioned closer to the target IMD than the other IMDs.

19. The method of claim 17, wherein the adaptively adjusting operation comprises incrementally decreasing the power of the transmission request over the first frequency band when the response analysis module receives one or more of the other signals from one of more the other IMDs.

20. The method of claim 17, wherein the adaptively adjusting operation comprises incrementally increasing the power of the transmission request over the first frequency band when the response analysis module does not receive the target response signal.

21. The device of claim 1, wherein the communication module, response analysis module and power adjustment module include at least one of a microprocessor, microcontroller, and an integrated circuit.

22. The system of claim 9, wherein the communication module, response analysis module and power adjustment module include at least one of a microprocessor, microcontroller, and an integrated circuit.

* * * * *

UNITED STATES PATENT AND TRADEMARK OFFICE
CERTIFICATE OF CORRECTION

Page 1 of 1

PATENT NO. : 9,232,485 B2
APPLICATION NO. : 13/974448
DATED : January 5, 2016
INVENTOR(S) : Wu et al.

It is certified that error appears in the above-identified patent and that said Letters Patent is hereby corrected as shown below:

Title Page, Item (72) Inventors, should read

-- (72) Inventors: YongjianWu, Saratoga, CA (US); Allan Schwartz, Thousand Oaks, CA (US); Gregory Hauck, Valencia, CA (US); Reza Shahandeh, Thousand Oaks, CA (US); Thanh Tieu, Simi Valley, CA (US) --.

Signed and Sealed this
Fifteenth Day of March, 2016

Michelle K. Lee
*Director of the United States Patent and Trademark Office*